(12) United States Patent
Fish et al.

(10) Patent No.: US 8,801,763 B2
(45) Date of Patent: Aug. 12, 2014

(54) SYSTEM FOR PROTECTION OF SOFT TISSUES AGAINST A TEETH WHITENING SUBSTANCE

(75) Inventors: David Andrew Fish, Haywards Heath (GB); Nigel David Young, Meadvale Redhill (GB); Jay Patel, Wembley (GB); Estelle Julie Dorothee Bernhard-Fichet, Cambridge (GB); Peter Douglas Fairley, Plymouth (GB)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/514,114

(22) PCT Filed: Dec. 2, 2010

(86) PCT No.: PCT/IB2010/055555
§ 371 (c)(1),
(2), (4) Date: Jun. 6, 2012

(87) PCT Pub. No.: WO2011/077299
PCT Pub. Date: Jun. 30, 2011

(65) Prior Publication Data
US 2012/0251971 A1    Oct. 4, 2012

Related U.S. Application Data

(60) Provisional application No. 61/289,638, filed on Dec. 23, 2009.

(51) Int. Cl.
*A61N 1/26* (2006.01)
(52) U.S. Cl.
USPC ............... 607/80; 433/27; 15/167.1; 607/79

(58) Field of Classification Search
USPC ...................... 433/27–32, 216, 229
See application file for complete search history.

(56) References Cited

U.S. PATENT DOCUMENTS

| | | | |
|---|---|---|---|
| 5,738,678 A * | 4/1998 | Patel | 433/29 |
| 5,894,620 A | 4/1999 | Polaert et al. | |
| 6,525,819 B1 * | 2/2003 | Delawter et al. | 433/29 |
| 7,467,946 B2 | 12/2008 | Rizoiu et al. | |

(Continued)

FOREIGN PATENT DOCUMENTS

| | | |
|---|---|---|
| WO | 9729714 A1 | 8/1997 |
| WO | 0016737 A1 | 3/2000 |
| WO | 2007073917 A1 | 7/2007 |
| WO | 2009042085 A1 | 4/2009 |

*Primary Examiner* — Cris L Rodriguez
*Assistant Examiner* — Matthew Seward (57) ABSTRACT

The appliance includes a brushhead having conductive fiber bristles by which a potential is applied to electrochemically activate a teeth whitening substance, such as peroxide, in the vicinity of the teeth. An impedance appliance system (62) or an optical appliance system (27) provides information concerning whether the conductive fiber bristles are adjacent a tooth surface or gum region. The impedance system uses an electrical signal through the fiber to determine the impedance of a circuit which includes the tooth or gum surface, the impedance being different, depending on whether a tooth or gum surface is in the circuit. The optical system generates a light beam which is directed to the mouth surface through a conductive fiber, the color of the returning light indicating whether the surface is a tooth or gum region. If a tooth is determined, the teeth whitening substance is activated at that bristle, while if gum tissue is determined, the teeth whitening substance is not activated at that bristle.

7 Claims, 5 Drawing Sheets

(56) References Cited

U.S. PATENT DOCUMENTS

| | | |
|---|---|---|
| 2001/0023057 A1* | 9/2001 | Alexander .................... 433/29 |
| 2004/0193235 A1 | 9/2004 | Altshuler et al. |
| 2005/0026103 A1 | 2/2005 | Wasylucha |
| 2005/0249677 A1 | 11/2005 | Malcmacher et al. |
| 2007/0009856 A1 | 1/2007 | Jones et al. |
| 2008/0003540 A1 | 1/2008 | Khawaled et al. |
| 2008/0060148 A1* | 3/2008 | Pinyayev et al. ............. 433/216 |
| 2008/0280248 A1 | 11/2008 | Pitts et al. |

\* cited by examiner

SYSTEM FOR PROTECTION OF SOFT TISSUES AGAINST A TEETH WHITENING SUBSTANCE

This invention relates generally to handheld appliances for whitening teeth, and more specifically concerns such an appliance which provides protection for the soft tissues of the mouth during the whitening process.

Teeth whitening systems and appliances are generally known, particularly in the professional arena. Whitening systems typically use peroxide or carbamide paste substances/formulations in conjunction with electrochemical activation or UV blue light activation to produce the whitening effect. However, due to the corrosive nature of the whitening formulations, restrictions on the strength of whitening products, particularly in the consumer market, are present to prevent damage to the soft tissues in the mouth, in particular the gum regions. The restrictions do, however, limit the efficacy of whitening treatments.

In the professional arena, more potent whitening formulations are permitted and used, but protective devices are used by the professional to shield the gums. Typically, the protection is in the form of a physical shield which fits over the gums, or a dental putty which is applied directly to cover the gums. The more potent whitening formulations used by professionals increases the efficacy of the whitening process as well as reduces treatment time. Training is necessary, however, in the professional arena for proper use of the whitening material.

Whitening formulations in the consumer arena, however, are often inconvenient, if not difficult to use, as well as not being very effective. Further, peroxide and other agents used in whitening formulations can come into contact with the gum regions and cause damage, if a high degree of care is not used. This contact with the gum tissue can occur in the professional arena as well, but more typically occurs in the consumer arena.

Hence, an appliance which is capable of using a whitening formulation which is effective for tooth whitening, but also provides reliable protection for the soft tissues, i.e. the gums, is desired.

Accordingly, the appliance for controlling the application of peroxide or other teeth whitening substance or formulation to the teeth of a user comprises: a system for measuring the impedance of a circuit which includes a conductive fiber from an appliance brushhead and a tooth or a gum region contacted by the conductive fiber and for determining whether the measured impedance includes a tooth or gum region; and a control circuit for preventing activation/generation of the peroxide or other teeth whitening substance or formulation in the vicinity of said fiber if the measured impedance includes a gum region and activating/generating the teeth whitening substance or formulation if the measured impedance includes a tooth.

An effective tooth whitening system for both consumer and professional use includes an appliance for delivering the tooth whitening formulation to the teeth in combination with an arrangement for protecting the soft tissues of the mouth, including particularly the gum regions, against contact by the tooth whitening substance/formulation, referred to hereinafter generally as formulations. In general, a tooth whitening substance, such as peroxide or carbmide, with a strength of 1% to 10%, is provided to the region of the teeth in a gel formulation either by the user or through the appliance. A variety of ways of providing the whitening formulation to the teeth are possible. The present protective arrangement is useful with a variety of whitening formulation delivery systems.

Figure 1:
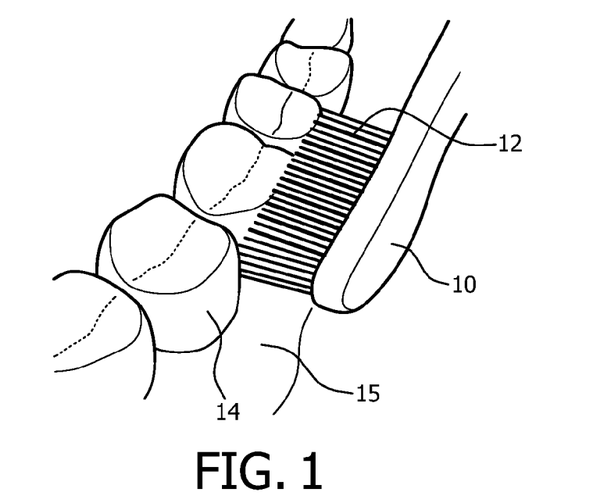
FIG. 1 is a schematic view showing a brushhead portion of a dental appliance positioned against the teeth of a user to accomplish whitening.
Figure 2:
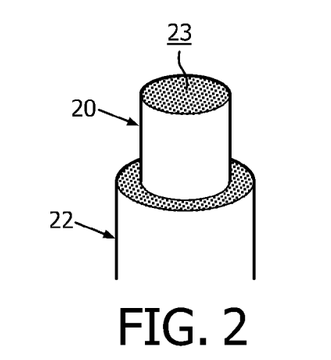
FIG. 2 is a simplified diagram of a bristle used in the present appliance

FIG. 1 shows a brushhead portion 10 of an appliance, such as a toothbrush, which includes a set of bristles 12. In FIG. 1, the bristles are positioned operatively against teeth 14 of a user. The whitening agent, shown at 15, in the gel formulation, such as peroxide, can be activated/generated electrochemically, in one example. This can be done with metallic or carbon fibers in the brushhead, with a voltage between pairs of electrodes in the range of −2 to 2 volts. Metallic or carbon cathode and anode fibers are present in brushhead 10. A single such fiber is shown in FIG. 2. Metallic or carbon (conductive) fibers 20 will usually be insulated by a polymer sheath 22 over most of its length, forming a bristle, with the tips 23 of metal such as platinum or other metal, or carbon, which may be preferred, exposed for approximately 1 mm, although this distance can vary. Alternatively, the sheath portions could extend slightly beyond the tip of the metal/carbon fibers, with the possible additional use of side hole access through the sheath to the metal or carbon element so that the electrical current between the cathode and anode fibers can produce the desired electrochemical activation of the whitening formulation. Alternatively, UV light can be used through transparent bristle fibers in order to provide initial or enhanced localized action of the whitening formulation.

As discussed above, one of the significant issues with teeth whitening is to maintain contact of the teeth whitening formulation only with the teeth to be whitened and to prevent contact of the formulation with gum (or other) tissue. It is thus important to be able to quickly and accurately determine whether the brushhead or a part thereof is adjacent a tooth surface or a gum surface. Two arrangements are shown and described herein to accomplish this important objective of a tooth whitening appliance, particularly for those for home (non-commercial) use, although the arrangements can be used in commercial (professional) appliances as well.

Figure 3:
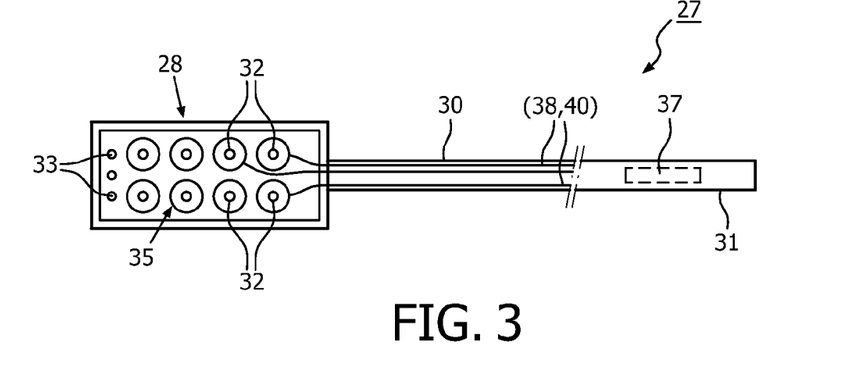
FIG. 3 is a top view of a brushhead and brush appliance stem for protection of soft tissues of one embodiment.

FIGS. 3, 4A-4C and 5 show an optical arrangement appliance 27 for preventing teeth whitening substance from coming into contact with soft (gum) tissue. FIG. 3 shows a brushhead 28 and toothbrush stem portion 30 of a toothbrush, which is connected to a handle 31. Brushhead 28 includes a plurality of active bristles 32-32. Each of the active bristles 32 includes an optical fiber 34, with an outer sheath 33. The active bristles can also typically include an electrochemical active region 35 for activating the whitening formulation, e.g. peroxide or other whitening substances, or the electrochemical activation could be accomplished by an adjacent fiber. A plurality of inactive bristles 33 (partially shown) around the periphery of the brushhead could be used to protect tissue at the side of the brushhead from contact with the teeth whitening formulation. Inactive bristles could also be used for scrubbing the teeth. Fibers 38 for carrying the optical signal and electrical wires 40 for carrying the electrical signal for activating the whitening formulation connect the brushhead bristle fibers with an optical detector and microprocessor control 37 in the handle of the toothbrush. Again, the optical function and the formulation activation can be accomplished in a single fiber.

Figure 4A:
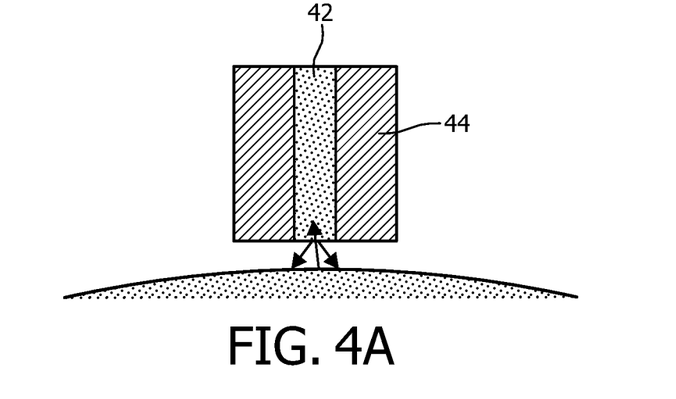
FIGS. 4A, 4B and 4C are simplified cross-section diagrams showing variations of fiber construction for the embodiment of FIG. 3.
Figure 4B:
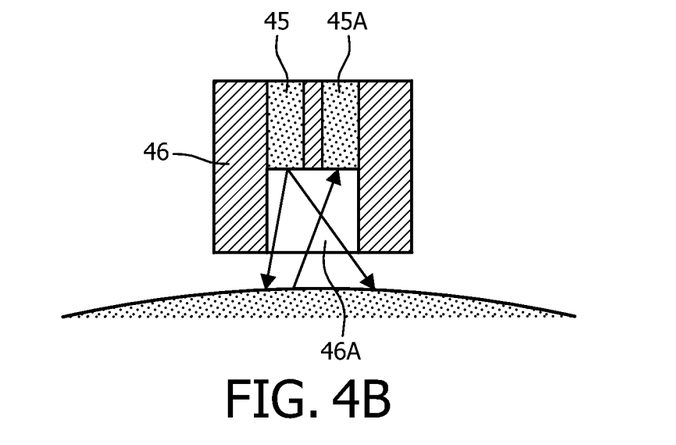
Figure 4C:
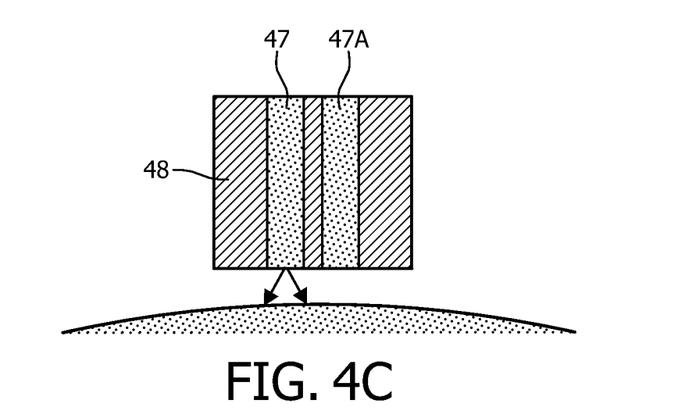

FIGS. 4A-4C show three alternatives for bristles 32 containing an optical fiber. FIG. 4A shows a single optical fiber 42 encompassed by a polymer sheath 44. In this arrangement, optical fiber 42, which is typically 0.1 mm in diameter, with a sheath diameter of 0.2-1 mm, come into contact with the tooth or gum surface. Electrochemically active regions can also provided in the bristle or in separate bristles. In operation of the appliance, light from a source will proceed down fiber 42 and contact the tooth or gum surface, with some light being reflected back into the fiber 42 and then through the stem to the optical detector which converts the returning optical signal into an electrical signal which is analyzed by control microprocessor 37. This arrangement uses a single fiber (channel). In some cases, however, light can be blocked from backscattering into the single fiber.

In another arrangement, shown in FIG. 4B, two optical fibers 45, 45A can be used in a single bristle sheath 46, with the fibers terminating a distance from the free end of the sheath. However, the bristle sheath may block the returning light; toothpaste which is captured within the exposed sheath volume 46A can also block returning light.

The arrangement of FIG. 4C shows a bristle with a double optical fiber arrangement 47, 47A, and a sheath 48, which could include electrochemically-active regions. In this arrangement, however, there is little backscattered light picked up. FIG. 4A thus appears to be the most desirable optical arrangement.

Figure 5:
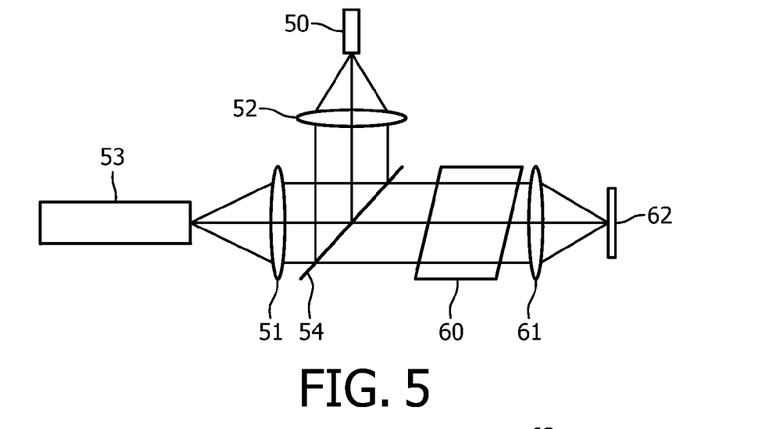
FIG. 5 is a diagram showing the structure and operation of the embodiment of FIG. 3.

FIG. 5 shows the optical detection structure 37 of the appliance of FIG. 3 in more detail. A white LED source 50 is provided in the handle of the toothbrush. The light from source 50 is directed through a lens 52 which collimates the light. The collimated light then proceeds to a beam splitter 54 with 50% of the light directed toward a focusing lens 51, which directs the light to the optical fibers 53 in the individual bristles, as shown in FIGS. 3 and 4A-4C. The remainder of the light from the beam splitter 54 is lost. The reflected light from the tooth or gum surface proceeds back through lens 56 and through beam splitter 54, which sends 50% of the light to dispersion optics 60, a lens 61, and then to a low pixel count CCD element 62. In this arrangement, if there are 8 fibers in the brushhead transmitting an optical beam, then for a 32×32 pixel CCD, each fiber has 16 pixels.

If the light impinges on a tooth surface, the returning light will be white, while if the light impinges on a gum surface, the returning light will be red. The CCD recognizes the difference in color. The output signal from the CCD is provided to the microprocessor which controls the electrochemical activation produced by the bristles through which light is returned, or by separate bristles. If the returning light is red, the potential to those bristles to accomplish the electrochemical process is turned off, so that the peroxide or other tooth whitening formulation in the vicinity of the active bristles is not activated, preventing activated whitening formulation from contacting and damaging the soft tissues. If the returning light is white, the potential to the activating bristles is turned on.

FIGS. 6-11 show another arrangement for controlling the application of a peroxide formulation or other teeth whitening formulation in the mouth to specific regions of the mouth, in particular, to just teeth surfaces, preventing activated whitening formulation from contacting the gums. This arrangement is an impedance-based technique for discriminating between conductive fibers on the brushhead making contact with a tooth surface or a gum surface. This arrangement permits accurate spatial control over the generation of peroxide or other teeth whitening formulation.

Figure 6:
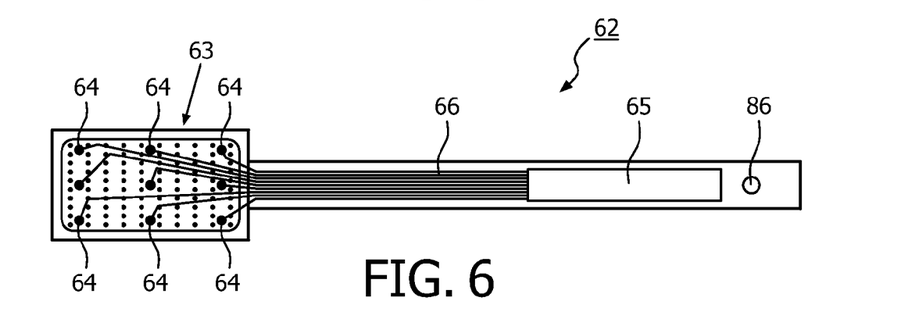
FIG. 6 is a top view of a dental appliance for whitening showing a brushhead construction for a second embodiment for protection of soft tissues.

The impedance embodiment makes use of the known fact that a tooth has a high impedance compared to the surrounding soft gum tissue. In FIG. 6, toothbrush appliance 62 is shown which includes a brushhead 63 with impedance measuring bristles 64 which are spaced over the area of the brushhead, and which are electrically connected to a measurement and control assembly 65 in the handle through a set of electrical connecting wires 66. The impedance-measuring bristles 64 are typically placed on or near the periphery of the brushhead to provide good spatial control of the activation of peroxide or other teeth whitening formulation over the area of brushhead 63. The electrical circuit impedance includes the impedance of the conductive fiber in the bristle contacting the surface. An on/off electrical feedback loop in the measurement and control circuit controls the application of the teeth whitening formulation activating potential at the tip of the electrochemical portion of the bristle which includes the conductive fiber.

Alternatively, to on-off activation, a pulse width modulation (PVM) control circuit can be used to control the rate of the activation/generation of the peroxide or other whitening formulation. A duty cycle with a long "on" pulse corresponds to a high rate of formulation activation/generation, while a short "on" pulse corresponds to a low rate of activation.

Typically, the conductive fiber used in measuring circuit impedance is contained in the same bristle which includes the element for activating the peroxide formulation electrochemically, thus giving localized control of where the peroxide is generated and what surface the peroxide contacts. In the instance where the conducting fiber tip of the bristle is in contact with soft gum tissue, a low electrical impedance will be measured, typically on the order of 50 kΩ while when a tooth surface is contacted a high impedance is measured, typically on the order of 50 kΩ. When a low impedance is measured, the feedback control 65 will reduce or turn off the potential on the tip of the electrical fiber, preventing activation of peroxide in that vicinity. Alternatively, generation of peroxide or other whitening formulation could be reversed, or the system switched to an alternate electrochemical mode.

The fibers/bristles in the impedance arrangement could also be inserted into a microtube which delivers the oxygenated teeth whitening gel at a defined flow rate to the tooth. The electrochemical action may be accomplished at a lower point on the fiber and the impedance sensing function accomplished by the tip of the fiber which would protrude from the tube. This could be accomplished by a single fiber/bristle by switching the function of the fiber between sensing and electrochemical action, or both functions can be accomplished with separate fibers within the tube. A separate reference fiber may be needed within the tube which could be silver or platinum. Two fiber electrodes could be used, one metallic and the other carbon, within a single tube, each fiber being partially insulated at some point along its length. Alternatively, the inside of the tube could be carbon or the tube made of carbon, with a partially insulated metal bristle inside.

Figure 7:
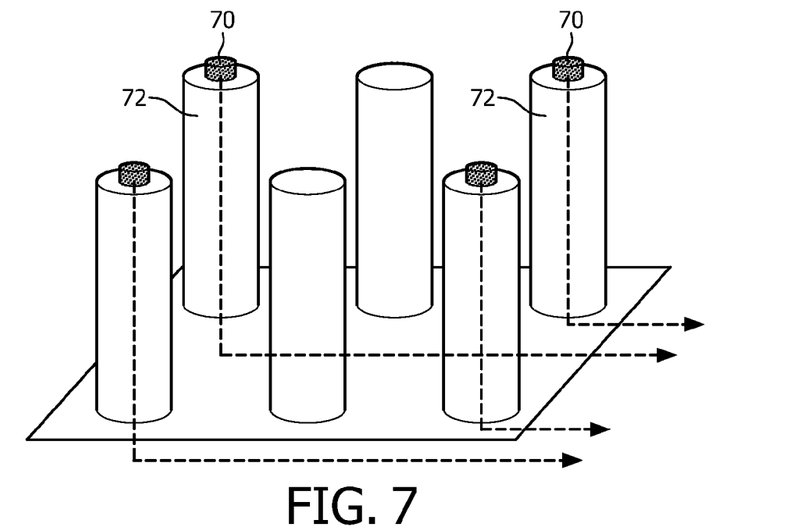
FIG. 7 is a diagram showing in more detail a portion of the brushhead of FIG. 6.
Figure 8:
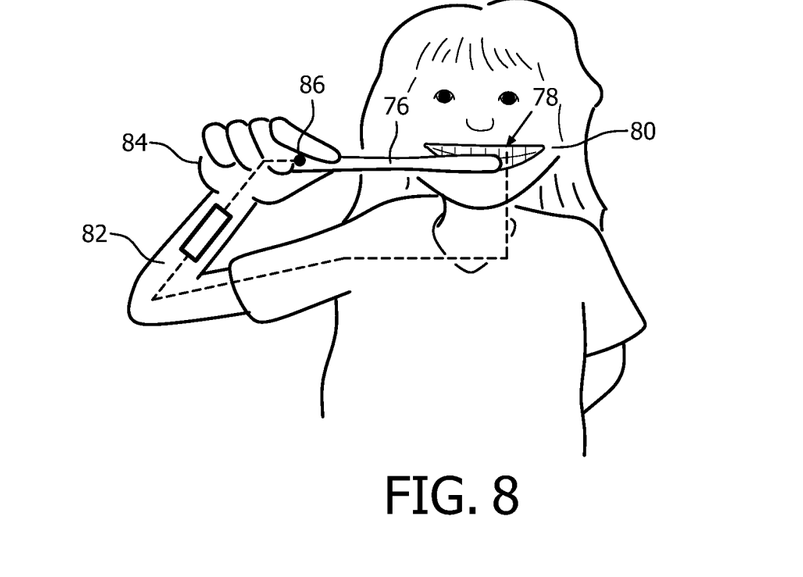
FIG. 8 shows a diagram of one operation of the embodiment of FIG. 6.

In this arrangement saliva is typically not very conductive, even though it contains various electrolytes, which prevents a short circuit in the mouth. Impedance measuring fibers can be distributed throughout the brushhead, as discussed above and as shown in FIG. 7, or they can be arranged in groups to provide more efficient tooth whitening over a larger surface. Since the measured impedance when the fiber is in contact with a tooth is significantly larger than when the fibers are in contact with the soft gum tissue, there is no difficulty in establishing a threshold impedance which is reliable in distinguishing the two situations for control of the electrochemical reaction. FIG. 7 shows some details of the bristle/fibers. The active bristles include conductive fibers 70 with a sheath 72. The conductive fibers 70 can be used for both the impedance measuring/sensing function as well as the electrochemical activation function in which a small potential, approximately −2 to 2 volts, is used to activate the teeth whitening formulation, such as peroxide, as discussed above. These two functions can also be accomplished by separate fibers. If the impedance measurement is small, indicating that the conductive fibers are contacting a gum surface, then the electric potential for the electrochemical activation is turned off by the control feedback circuit.

Figure 9:
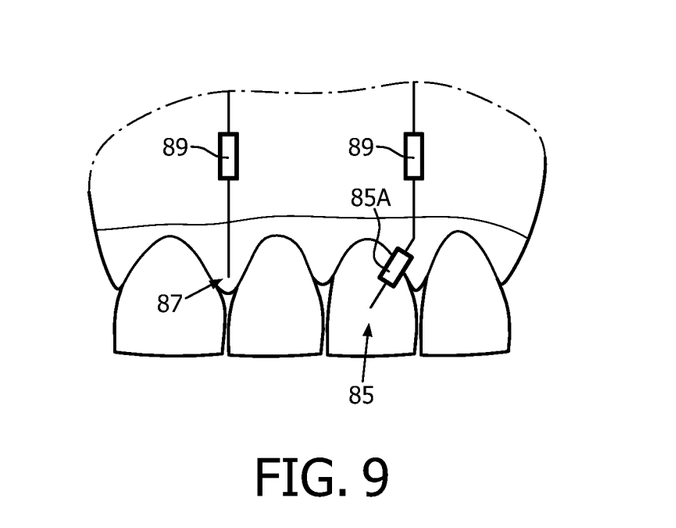
FIG. 9 is an electrical diagram for the embodiment of FIG. 6.

In one embodiment, referring to FIGS. 8-11, the measured impedance circuit includes the conductive fiber in the bristle 76, the tooth or gum surface referred to at 78, the head of the user 80, the arm of the user 82 and the hand of the user 84 which contacts a reference electrode pad 86 on the handle of the appliance. Again, if this impedance measurement is large, on the order of 100 kΩ or greater, then a tooth surface contact is indicated, while if impedance is relatively small, typically on the order of 50 kΩ or less, a gum surface contact by the bristle is indicated. FIG. 9 shows the two contact circuits, a tooth 85 and its impedance represented by 85A and the impedance of the body 89, or a gum region 87 and the impedance of the body 89.

Figure 10:
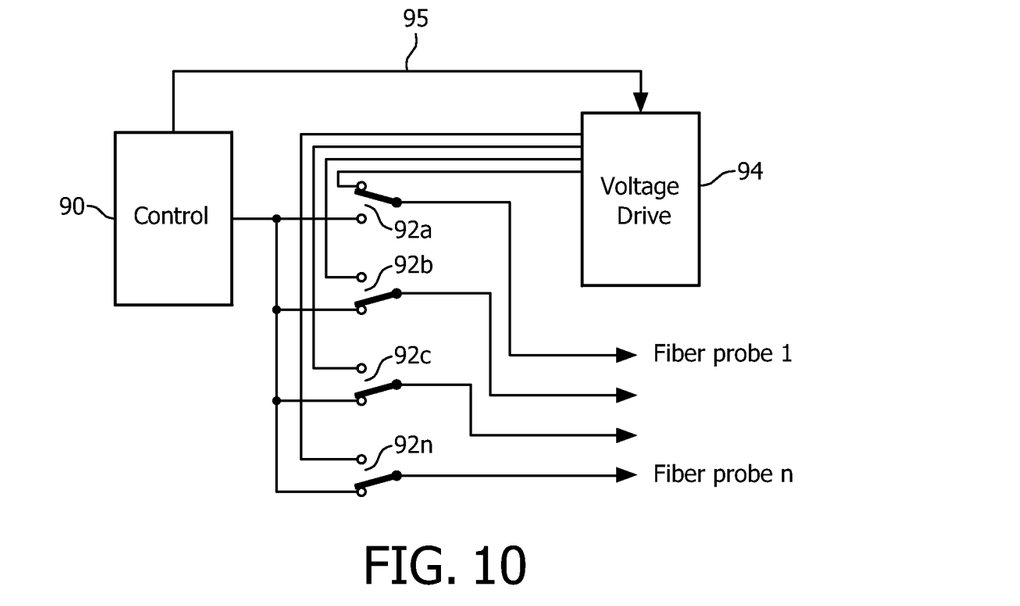
FIG. 10 is a diagram showing the embodiment of FIG. 6 which involves both the whitening process and the protection of the soft tissues with a plurality of bristles.

FIG. 10 shows a simplified circuit diagram of a multiplex assembly 91 which makes use of all of the bristles in the brushhead containing conductive fibers. The impedance measuring control assembly 90 sequentially closes switches 92a-n, one for each conductive fiber in the brushhead, in sequence. An impedance measurement is then made for each fiber in turn. The switches are then sequentially switched to the electrochemistry voltage drive unit 94, using a feedback line 95, which applies the activation voltage to the fibers for the electrochemical reaction to produce the activated peroxide or other teeth whitening formulation.

Figure 11:
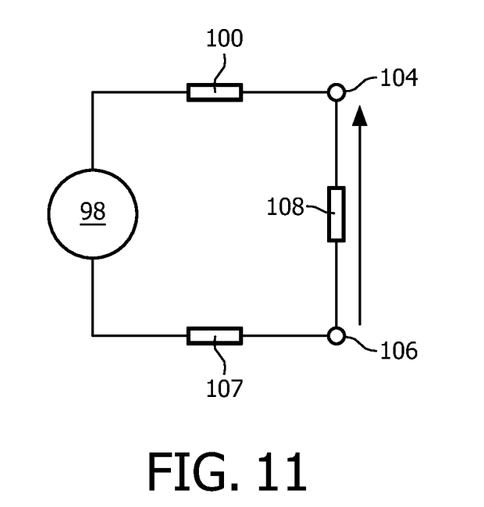
FIG. 11 shows a circuit implementation for the embodiment of FIG. 6.

A simplified circuit implementation is shown in FIG. 11. For example, a 10 KHz, 100 mV AC signal 98 is applied to an impedance circuit which includes a sensing resistance 100, a point of contact 104 of the tooth or gum surface by the conductive element, a reference pad 106 on the handle, the impedance of the body 107 and the impedance of the tooth or the gum, represented at 108. If the impedance 108 is high, a tooth surface is indicated and a voltage is applied through the conductive tip to initiate the electrochemical reaction, while if the impedance 108 is low, indicating a contact with soft gum tissue, the voltage is not applied.

In another embodiment, the impedance measurement is made between two separate conductive bristle elements, such that the impedance circuit comprises a first conductive bristle element 1, the impedance of the tooth surface or the gum surface and the second conductive bristle element. The difference in total impedance between the gum contact and a tooth contact is again substantial enough so that the electrochemical potential for the probe can be reliably either turned on to activate the whitening formulation or turned off, to prevent such activation.

Accordingly, an appliance has been disclosed which is constructed and arranged to protect the soft tissue such as the gums from contact by peroxide or other substance used to whiten the teeth. This is accomplished by using brushhead bristles to identify the surface which they are contacting. This is done by an optical technique impedance or an impedance technique. In either case, a determination is made as to which surface the bristles are in contact with, and the potential for activating the peroxide or other teeth whitening substance is either turned or turned off, thereby protecting the soft tissues.

Although a preferred embodiment has been disclosed for purposes of illustration, it should be understood that various changes and modifications and substitutions could be made in the preferred embodiment without departing from the spirit of the invention as defined by the claims which follow:

The invention claimed is:

1. An appliance for controlling an application of peroxide or other teeth whitening substance to a user's teeth, the appliance comprising:
   a source of light;
   a system for directing the light from the source of light through an optical fiber within an active bristle on an appliance brushhead to a surface in the mouth which is either a tooth or a gum region;
   a detection system for determining a selected characteristic of a returning reflected light from the mouth surface via the optical fiber within the active bristle, wherein one aspect of the characteristic indicates that the returning reflected light is reflected from a tooth and another aspect of the characteristic indicates that the returning reflected light is reflected from a gum region; and
   a control circuit for (i) activating the tooth whitening substance if the characteristic is the one aspect, and (ii) not activating the tooth whitening substance if the characteristic is the another aspect, wherein the control circuit activates the tooth whitening substance by sending an electrical signal to an electrochemical active region on the (a) the active bristle, through which the returning reflected light is returned, or (b) a bristle fiber, adjacent thereto.

2. The appliance of claim 1, wherein the characteristic is color.

3. The appliance of claim 2, wherein one color is white and another color is red.

4. The appliance of claim 1, wherein the appliance includes a beam splitter, a plurality of lenses and a detector for directing and focusing the light from the light source to the optical fiber, and then directing at least a portion of the returning reflected light to the detector for converting an optical signal of the returning reflected light into an electrical signal.

5. The appliance of claim 1, wherein the brushhead includes a plurality of active bristles, wherein each active bristle includes an optical fiber, and a plurality of inactive bristles around the periphery of the brushhead.

6. The appliance of claim 1, wherein the teeth whitening substance comprises one selected from the group consisting of peroxide and carbamide.

7. The appliance of claim 1, wherein the detection system further comprises a first dimension-by-a second dimension pixel CCD element that recognizes a difference in the characteristic between the one aspect and the another aspect, wherein each optical fiber of an active bristle corresponds with a given number of pixels of the first dimension-bysecond dimension pixel CCD element, and wherein the control circuit is responsive to an output signal of the CCD element.

* * * * *